United States Patent [19]

Cohen et al.

[11] Patent Number: 4,902,691

[45] Date of Patent: Feb. 20, 1990

[54] HETEROALKYLAMIDES OF (8-β)-1-ALKYL-6-(SUBSTITUTED)ERGOLINES USEFUL FOR BLOCKING 5HT$_2$ RECEPTORS

[75] Inventors: Marlene L. Cohen, Indianapolis; David W. Robertson, Greenwood, both of Ind.

[73] Assignee: Eli Lilly and Company, Indianapolis, Ind.

[21] Appl. No.: 286,192

[22] Filed: Dec. 19, 1988

[51] Int. Cl.$^4$ .................... A61K 31/48; C07D 457/06; C07D 401/14

[52] U.S. Cl. ........................... 514/288; 546/69

[58] Field of Search ........................... 546/69; 514/288

[56] References Cited

U.S. PATENT DOCUMENTS

| | | | |
|---|---|---|---|
| 2,997,470 | 8/1961 | Pioch | 260/247.2 |
| 3,228,944 | 1/1966 | Bernardi et al. | 260/285.5 |
| 3,904,633 | 9/1975 | Mago nee Karacsony et al. | 260/285.5 |
| 4,101,552 | 7/1978 | Mago nee Karacsony et al. | 260/285.5 |

FOREIGN PATENT DOCUMENTS

| | | |
|---|---|---|
| 125498 | 7/1967 | Czechoslovakia . |
| 2108502 | 5/1983 | Fed. Rep. of Germany . |
| 982737 | 2/1965 | United Kingdom . |

OTHER PUBLICATIONS

Chemical Abstracts 106:5306w (1987).
Chemical Abstracts 77:34752b (1972).
Chemical Abstracts 65:3924f (1966).

*Primary Examiner*—Mukund J. Shah
*Assistant Examiner*—Cecilia Shen
*Attorney, Agent, or Firm*—Robert A. Conrad; Leroy Whitaker

[57] ABSTRACT

This invention provides (8β)-N-heteroalkyl-1-alkyl-6-(substituted)ergoline-8-carboxamides useful for blocking 5HT$_2$ receptors in mammals having an excess of serotonin centrally or peripherally. The invention also provides methods for treating sexual dysfunction, hypertension, migraine, vasospasm, thrombosis, ischemia, depression, anxiety, sleep disorders and appetite disorders with a compound of the invention.

25 Claims, No Drawings

HETEROALKYLAMIDES OF (8-β)-1-ALKYL-6-(SUBSTITUTED)ERGOLINES USEFUL FOR BLOCKING 5HT₂ RECEPTORS

SUMMARY OF THE INVENTION

The present invention relates to a compound of the formula

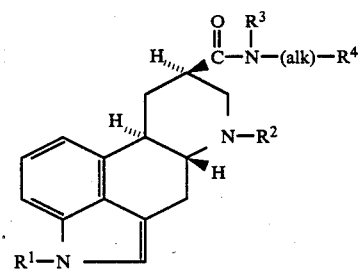

wherein:
$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is pyridinyl or imidazolyl;
alk is a divalent organic radical derived from a straight or branched $C_1$-$C_5$ alkane; and
the pharmaceutically acceptable acid addition salts thereof.

The present invention also provides pharmaceutical formulations comprising, and methods of using, compounds of the invention.

DETAILED DESCRIPTION OF THE INVENTION

In the above formula, the term "$C_1$-$C_4$ alkyl" represents a straight or branched alkyl chain having from one to four carbon atoms. Typical $C_1$-$C_4$ alkyl groups include methyl, ethyl, n-propyl, isopropyl, n-butyl, sec.-butyl and the like.

"$C_1$-$C_4$ straight chain alkyl" represents a straight, but not branched, alkyl chain having from one to four carbon atoms. "$C_1$-$C_4$ Straight chain alkyl" groups are methyl, ethyl, n-propyl and n-butyl.

The term "pyridinyl" is 2-, 3-, or 4-pyridinyl. The term "imidazolyl" refers to 1-, 2-, or 4-imidazolyl.

The term "alk" refers to a divalent organic radical derived from a straight or branched $C_1$-$C_5$ alkane. Such groups include —$CH_2$—, —$CH(CH_3)$—, —$C(CH_3)_2$—, —$CH(C_2H_5)$—, —$CH_2CH_2$—, —$CH_2CH(CH_3)$—, —$CH(CH_3)CH_2$—, —$CH(CH_3)CH(CH_3)$—, —$CH_2C(CH_3)_2$—, —$CH_2CH(C_2H_5)$—, —$CH_2CH_2C$-$H_2$—, —$CH(CH_3)CH_2CH_2$—, —$CH_2CH(CH_3)CH_2$—, —$CH_2CH(C_2H_5)CH_2$—, —$CH_2CH_2CH(C_2H_5)$—, —$C(CH_3)_2CH_2CH_2$—, —$CH(CH_3)CH_2CH(CH_3)$—, —$CH_2CH_2CH_2CH_2$—, —$CH_2C(CH_3)_2CH_2$—, —$CH_2CH_2CH_2CH_2CH_2$—, and the like.

While all of the compounds of the present invention are believed useful for blocking 5HT₂ receptors in mammals, certain of the compounds are preferred for such use. Preferably, $R^1$ is isopropyl. Also, $R^2$ is preferably methyl, $R^3$ is hydrogen, alk is —$CH_2$— or —$CH_2CH_2$— and $R^4$ is 2- or 3- pyridinyl. Other preferred aspects of the present invention will be noted hereinafter.

Compounds of the present invention are named as ergoline derivatives in which the trans(−) or 5R,10R configuration of the bridgehead hydrogens is specified. This is the same configuration as in the naturally-occurring 9,10-dihydro ergot alkaloids. In U.S. Pat. No. 3,580,916, a different naming system is used. The basic ring system is named as a 6aR,10aR-4,6,6a,7,8,9,10,10a-octahydroindolo[4,3-f,g]quinoline. Illustratively, by the alternate naming system, 9,10-dihydrolysergic acid becomes 6aR,10aR-7-methyl-4,6,6a,7,8,9,10,10a-octahydroindolo[4,3-f,g]quinoline-9β-carboxylic acid. Another equally valid name for acid is (8β)-6-methylergoline-8-dihydrolysergic carboxylic acid. The trivial name "ergoline" will be employed herein with the numbering system specified above for compounds of the invention.

Pharmaceutically-acceptable acid addition salts of the compounds of the invention include salts derived from non-toxic inorganic acids such as hydrochloric acid, nitric acid, phosphoric acid, sulfuric acid, hydrobromic acid, hydriodic acid, phosphorous acid and the like, as well as salts derived from non-toxic organic acids such as aliphatic mono- and dicarboxylic acids, phenyl-substituted alkanoic acids, alkandioic acids, aromatic acids, aliphatic and aromatic sulfonic acids, and the like. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1.4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and like salts.

The following examples further illustrate specific compounds of the present invention:
(8β)-N-[(1H-Imidazol-1-yl)methyl]-1-isopropyl-6-n-butyl-ergoline-8-carboxamide
(8β)-N-[2-(1H-Imidazol-2-yl)ethyl]-1-sec.-butyl-6-methylergoline-8-carboxamide maleate
(8β)-N-[3-(1H-Imidazol-4-yl)propyl]-1,6-diethylergoline-8-carboxamide nitrate
(8β)-N-[4-(2-Pyridinyl)butyl]-N-ethyl-1-isopropyl-6-methylergoline-8-carboxamide
(8β)-N-[5-(3-Pyridinyl)pentyl]-1-isopropyl-6-methylergoline-8-carboxamide hydrochloride
(8β)-N-[(4-Pyridinyl)methyl]-N-methyl-1-isopropyl-6-n-propylergoline-8-carboxamide
(8β)-N-[1-(1H-Imidazol-1-yl)ethyl]-1-t-butyl-6-n-propylergoline-8-carboxamide
(8β)-N-[1-(1H-Imidazol-2-yl)propyl]-1-t-butyl-6-methylergoline-8-carboxamide succinate
(8β)-N-[1-(1H-Imidazol-4-yl)butyl]-1-ethyl-6-methylergoline-8-carboxamide citrate
(8β)-N-[1-(2-Pyridinyl)pentyl]-1-sec.-butyl-6-methylergoline-8-carboxamide lactate
(8β)-N-[2-(3-Pyridinyl)propyl])-N-n-propyl-1-isopropyl-6-methylergoline-8-carboxamide
(8β)-N-[2-(4-Pyridinyl)butyl]-N-methyl-1-n-butyl-6-n-butylergoline-8-carboxamide
(8β)-N-[2-(1H-Imidazol-1-yl)pentyl]-1-iso-propyl-6-n-allylergoline-8-carboxamide acetate
(8β)-N-[3-(1H-Imidazol-2-yl)butyl]-1-iso-propyl-6-methylergoline-8-carboxamide (8β)-N-[3-(1H-Imidazol-4-yl)pentyl]-1-n-propyl-6-methylergoline-8-carboxamide maleate
(8β)-N-[4-(2-Pyridinyl)pentyl]-1,6-di(n-propyl)ergoline-8-carboxamide
(8β)-N-[(3-pyridinyl)methyl]-N-methyl-1,6-dimethylergoline-8-carboxamide
(8β)-N-[2-(4-Pyridinyl)ethyl]-1,6-diethylergoline-8-carboxamide
(8β)-N-[3-(1H-Imidazol-1-yl)propyl]-1-iso-propyl-6-ethylergoline-8-carboxamide hydrobromide
(8β)-N-[4-(1H-Imidazol-2-yl)butyl]-1-n-butyl-6-methylergoline-8-carboxamide malonate
(8β)-N-[5-(1H-Imidazol-4-yl)pentyl]-1-n-butyl-6-n-propylergoline-8-carboxamide
(8β)-N-[3-(2-Pyridinyl)-1,1-dimethylpropyl]-1-n-butyl-6-methylergoline-8-carboxamide
(8β)-N-[3-(3-Pyridinyl)-1,2-dimethylpropyl]-N-methyl-1-n-propyl-6-methylergoline-8-carboxamide
(8β)-N-[3-(4-Pyridinyl)-1-methylbutyl]-N-methyl-1-isopropyl-6-allylergoline-8-carboxamide
(8β)-N-[3-(1H-Imidazol-1-yl)-2-methylbutyl]-1-sec.-butyl-6-methylergoline-8-carboxamide tartrate
(8β)-N-[3-(1H-Imidazol-2-yl)-1-methylpropyl])-1-iso-propyl-6-n-butylergoline-8-carboxamide
(8β)-N-[2-(1H-Imidazol-4-yl)pentyl]-1-methyl-6-methylergoline-8-carboxamide oxalate
(8β)-N-[3-(3-(2-Pyridinyl)pentyl]-N-n-propyl-1-methyl-6-n-propylergoline-8-carboxamide
(8β)-N-[4-(3-Pyridinyl)pentyl]-1-t-butyl-6-methylergoline-8-carboxamide
(8β)-N-[3-(4-Pyridinyl)-2,2-dimethylpropyl]-1,6-diethylergoline-8-carboxamide
(8β)-N-[2-(1H-Imidazol-1-yl)-1,1-dimethyl]-1-isopropyl-6-n-propylergoline-8-carboxamide maleate
(8β)-N-[2-(1H-Imidazol-2-yl)-1-methylethyl]-1-isopropyl-6-methylergoline-8-carboxamide suberate
(8β)-N-[3-(1H-Imidazol-4-yl)-1-ethylpropyl]-1-n-propyl-6-allylergoline-8-carboxamide
(8β)-N-[2-(2-Pyridinyl)-1-methylpropyl]-N-methyl-1-n-butyl-6-methylergoline-8-carboxamide citrate
(8β)-N-[3-(3-pyridinyl)-1-methylbutyl]-N-n-butyl-1-isopropyl-6-methylergoline-8-carboxamide
(8β)-N-[4-(4-pyridinyl)-2-methylbutyl]-N-ethyl-1-isopropyl-6-methylergoline-8-carboxamide hydroxide The compounds of the present invention may be prepared by a variety of procedures well known to those of ordinary skill in the art. Preferably, for compounds wherein R² is methyl, dihydrolysergic acid is converted to the alkali metal salt and then to the (C₁–C₄ alkyl)formate derivative. This compound is finally reacted with the appropriate heteroalkylamine to provide a compound of the invention. This reaction is represented by the following scheme.

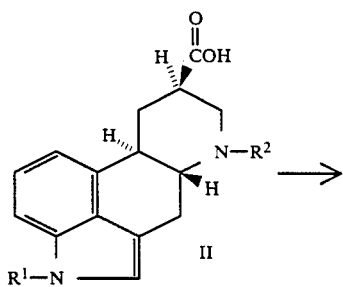

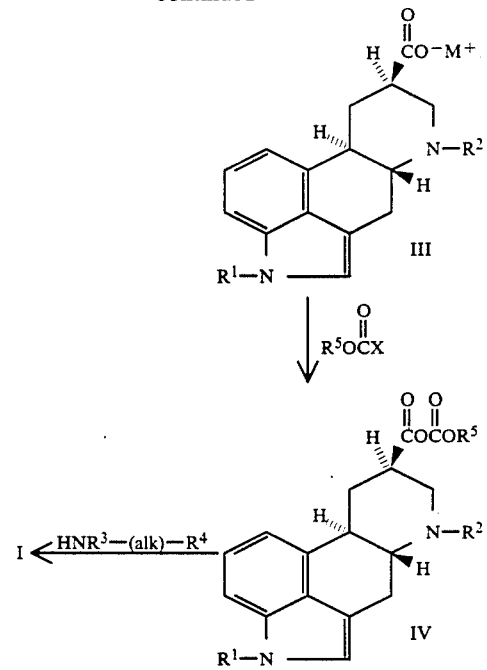

wherein $R^1$, $R^2$, $R^3$, $R^4$, alk, and m are as defined above, $R^5$ is $C_1$–$C_4$ alkyl, such as methyl, ethyl or preferably isobutyl, X is halogen, especially chloro, and M is an alkali metal.

The reaction can be carried out by combining the dihydrolysergic acid derivative II with about an equimolar quantity to slight excess of the base containing an alkali metal in a mutual solvent such tetrahydrofuran, diethyl ether, dichloromethane, dioxane, dimethylsulfoxide, N,N-dimethylformamide (DMF), benzene, toluene, and the like. Commonly used bases include sodium or potassium hydride, sodium carbonate and especially potassium carbonate. This mixture is typically heated to form the alkali metal salt intermediate III. The mixture is next cooled and an equimolar to slight excess of a $C_1$–$C_4$ alkyl haloformate is added to the reaction mixture. After sufficient time to form the ($C_1$–$C_4$ alkyl)formate intermediate IV, typically approximately five to about 30 minutes, at least one equivalent of the desired heteroalkylamine is added to the reaction mixture. Generally, the reaction is substantially complete after about two to about 200 hours when carried out at a temperature of about −40° to about 50° C., preferably from about −20° to about 25° C. The product of the reaction may be isolated by simply removing the reaction solvent, for instance by evaporation under reduced pressure. More typically, the reaction mixture containing the free base of the desired compound may be combined with water, and the product collected by filtration or extracted into a water immiscible solvent. The product thus isolated can be further purified if desired by any of several well known techniques.

If the desired final product is not a 9,10-dihydrolysergic acid amide, that is, not a (8β)-6-methylergoline-8-carboxamide, but is a 6-ethyl, 6-n-propyl, 6-n-butyl, or the like derivative, the replacement of the 6-methyl group must take place prior to the amidation procedure described above. In this procedure, it is preferable to use a lower alkyl (such as methyl or ethyl) ester of a 9,10-dihydrolysergic acid. Replacement of the 6-methyl group with ethyl, n-propyl, n-butyl, or the like, can be carried out by the procedure of Kornfeld and Bach, U.S. Pat. No. 4,166,182, whereby the N-methyl group is reacted with cyanogen bromide to form an N-cyano derivative. The cyano group can be removed by hydrogenation using zinc dust and hydrochloric acid. Alternatively, basic hydrolysis can be used. Either procedure provides a secondary amine group at the 6-position, but also a free 8β-carboxylic acid since the hydrolysis also saponifies the 8β-lower alkyl ester group. Next, the 6-position is alkylated or allylated under standard conditions followed by amidation with the desired heteroalkylamine. This procedure is graphically illustrated by the following reaction scheme:

group under the preferred basic conditions yields a (8β)-6-methylergoline-8-carboxylic acid (IX). The ring nitrogen at $N_5$ is then realkylated with a $C_1$-$C_4$ alkyl halide or allyl halide in the presence of base under standard conditions to provide intermediates of Formula II. Finally, the acid is converted to the amide with a desired heteroalkylamine by the procedures herein described, such as with a coupling reagent such as N,N'-dicyclohexylcarbodiimide or carbonyldiimidazole to yield the compounds of this invention.

It might seem Sisyphean to realkylate at $N^6$ with a methyl group since that group is present in the 9,10-dihydrolysergic acid starting material. However, the process would enable one to insert a "tagged" ($^{14}C$ or

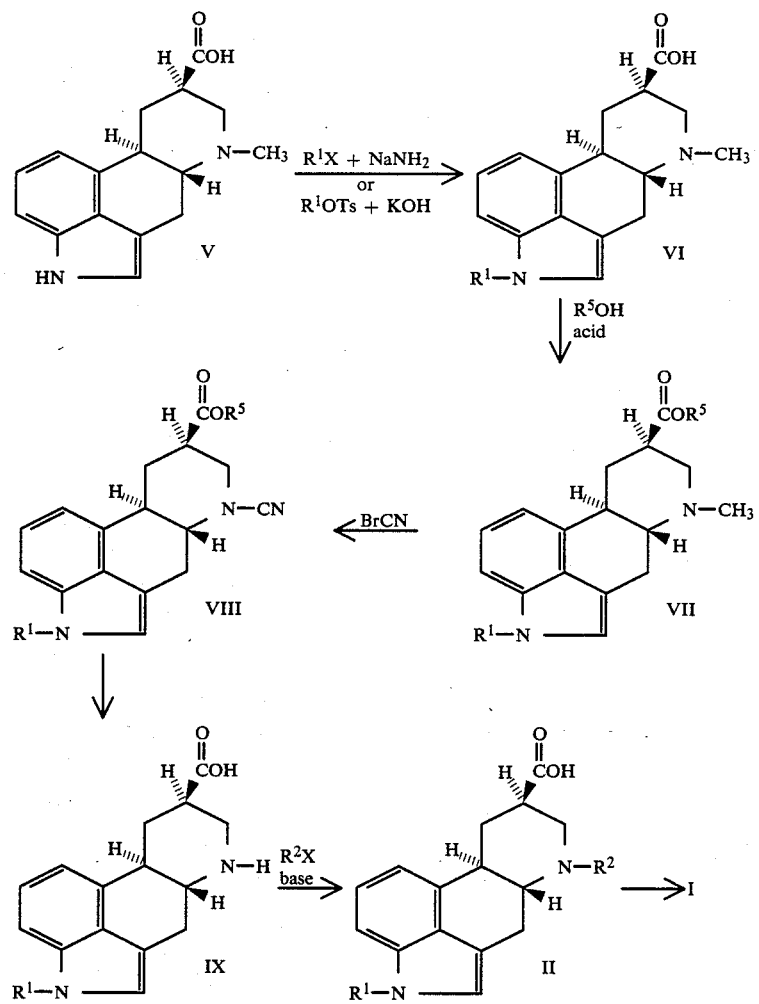

wherein $R^1$, $R^2$, $R^3$, $R^4$ and m are as defined above, $R^5$ is $C_1$-$C_4$ alkyl and X is a good leaving group such as halo or a sulfonate derivative.

More specifically, in the above reaction scheme, 9,10-dihydrolysergic acid (V) is alkylated on the indole nitrogen with a primary or secondary $C_1$-$C_4$ %kalkyl halide using sodamide to create the reactive anion, or preferably using an aryl sulfonate such as a p-tosylate in the presence of potassium hydroxide in DMSO. The N-1 product (VI) is then esterified with a lower alkanol $R^5OH$ (a $C_1$-$C_2$ alkanol preferably) to yield the ester (VII). This intermediate is then reacted with BrCN by standard procedures to replace the methyl group and form a 6-cyano derivative (VIII). Removal of the cyano $^3H$) methyl group into the compound for metabolic or receptor binding studies.

The compounds of the present invention may also be prepared by the reaction of a 1-alkyl-6-(substituted)ergoline-8-hydrazide with the desired cycloalkylamine under conditions well known to those of ordinary skill in the art. This reaction may be represented by the following scheme:

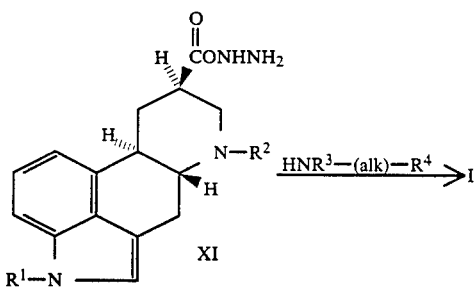

wherein $R^1$, $R^2$, $R^3$, $R^4$, alk, and m are as defined above.

According to this procedure, the hydrazide starting material XI is dissolved in an aqueous acidic solution and the resulting mixture is cooled to a temperature in the range of about 0° C. to about 20° C. Typical acids suitable for use in this step of the process include the hydrohalic acids, such as hydrobromic acid and hydroiodic acid, and especially hydrochloric acid. To this mixture is added either sodium nitrite or sodium periodate, typically in an excess amount, and the mixture is made basic with a suitable base such as the inorganic bases, especially sodium bicarbonate. The intermediate formed by this reaction is isolated by extraction with a water immisible organic solvent, and an equimolar, to preferably an excess, of the desired heteroalkylamine is combined with the solution containing the intermediate. The reaction is substantially complete within about one to 24 hours when conducted at a temperature in the range of about 0° C. to about 100° C., more preferably within about four to 12 hours when conducted at a temperature in the range of about 5° C. to about 20° C. The product is then isolated, typically by decanting or evaporating the volatile constituents under vacuum. The isolated product may then be further purified, if desired, by standard procedures.

The compounds of the present invention may also be prepared by the direct coupling of a (8β)-1-alkyl-6-(substituted)ergoline-8-carboxylic acid derivative with an appropriate heteroalkylamine in the presence of a coupling reagent to provide the corresponding (8β)-1-alkyl-6-(substituted)ergoline-8-carboxamide. This reaction may be represented by the following scheme:

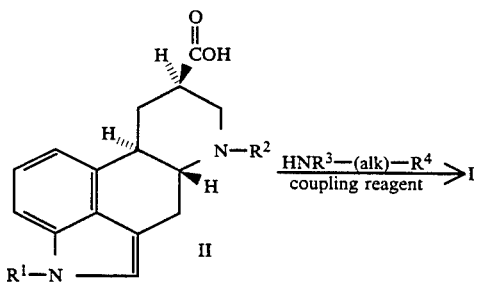

wherein $R^1$, $R^2$, $R^3$, $R^4$, alk, and m are as defined above.

This reaction process necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as 1-hydroxybenzotriazole mesylate or N-ethoxycarbonyl-2-ethoxy-1,2-dihydroquinoline (EEDQ). The direct coupling of a (8β)-1-alkyl-6-(substituted)ergoline-8-carboxylic acid II and a heteroalkylamine is carried out by adding about an equimolar quantity of the amine starting material to a solution of the carboxylic acid in the presence of an equimolar quantity to slight excess of the coupling reagent. The reaction generally is carried out in an unreactive organic solvent such as dichloromethane, tetrahydrofuran (THF) or N,N-dimethylformamide (DMF), and is typically complete within about twenty-four hours when conducted at a temperature of about 0° to about 30° C. The product is then typically isolated by filtration. The (8β)-1-alkyl-6-(substituted)ergoline-8-carboxamide thus formed can be further purified, if needed, by any of several routine methods, including crystallization from common solvents, chromatography over solid supports such as silica or alumina, and related purification techniques.

Amide formation can also be accomplished by converting acid II to the corresponding acid chloride followed by reaction with $HNR^3$-(alk)-$R^4$. The acid halide of a (8β)-1-alkyl-6-(substituted)-ergoline-8-carboxylic acid II is generated from the acid through the use of a suitable reagent such as thionyl chloride, oxalyl chloride, or phosphorus oxychloride in an unreactive solvent such as dichloromethane, tetrahydrofuran (THF) or N,N-dimethylformamide (DMF). An equimolar quantity to slight excess of the reagent is used, and the acid halide formation is typically complete within about twenty-four hours when conducted at a temperature of about −25° to about 30° C. The heteroalkylamine is then added, preferably along with an acid scavenger such as an alkali metal carbonate, triethylamine, or pyridine. Generally, amide formation is substantially complete after about two to about 200 hours when conducted at a temperature of about −40° to about 50° C., preferably from about −20° to about 25° C. The product of the reaction may be isolated by simply removing the reaction solvent, for instance by evaporation under reduced pressure. More typically, the reaction mixture containing the free base of the desired compound may be combined with water, and the product collected by filtration or extracted into a water immiscible solvent. The product thus isolated can be further purified if desired by any of several well-known techniques.

The preparation of the ergoline compounds which are intermediates to the compounds of the present invention is well known to those of ordinary skill in the art. According to this procedure, dihydrolysergic acid is first alkylated on the N-1 nitrogen atom with an alkyl halide in the presence of base. Liquid ammonia is a convenient solvent with sodamide as the preferred base. An alternate alkylation procedure whereby a sulfonate derivative is used in the presence of an alkali metal hydroxide is more fully described in the pending U.S. application Ser. No. 782,339, filed Oct. 1, 1985, of Marzoni. According to this procedure, an arylsulfonate of the structure R-O-SO$_2$-phenyl-Y, wherein Y is H, 4-CH$_3$, 4-Br or 4-NO$_2$ is reacted with an ergoline-8-carboxylic acid in a suitable solvent, conveniently DMSO, in the presence of base, preferably sodium or potassium hydroxide.

To synthesize compounds wherein the 6-position is other than methyl, that is, the compound possesses a 6-ethyl, 6-n-propyl, 6-n-butyl substituent, or the like derivative, the replacement of the 6-methyl group will take place prior to the final amidation as described above.

The pharmaceutically acceptable acid addition salts of the invention are typically formed by reacting an amine of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods of their synthesis. The Examples are not intended to be limiting to the scope of the invention in any respect and should not be so construed.

EXAMPLE 1

(8β)-N-[2-(1H-Imidazol-4-yl)ethyl]-1-isopropyl-6-methylergoline-8-carboxamide

To a mixture of 3.5 g of (8β)-1-isopropyl-6-methylergoline-8-carboxylic acid in 80 ml of dimethylformamide were added 2.27 g of 1,1'-carbonyldiimidazole. After stirring for 3 hours at room temperature, the mixture was added dropwise to a solution of 2.27 g of histamine dihydrochloride in 100 ml of dimethylformamide to which 3.6 ml of triethylamine had been added. The reaction mixture was stirred at room temperature overnight and then poured into 2 liters of ice water to which 5 ml of ammonium hydroxide had been added. The resulting precipitate was recovered by filtration. The solid material was crystallized from methanol/water to provide 2.41 g of the desired title product hemihydrate as a light pink powder, m.p. 83°–86° C.

Analysis for $C_{24}H_{31}N_5O.0.5\ H_2O$: Calc.: C, 69.54; H, 7.78; N, 16.89; Found: C, 69.92; H, 7.68; N, 16.62.

EXAMPLES 2–13

The following compounds were prepared according to the procedure of Example 1 employing the appropriate ergolinecarboxylic acid and the corresponding amine.

2. (8β)-N-[3-(1H-Imidazol-1-yl)propyl]-1-isopropyl-6-methylergoline-8-carboxamide dihydrate, 69% yield, m.p.=75°–79° C.

Analysis for $C_{25}H_{33}N_5O.2\ H_2O$: Calc.: C, 65.91; H, 8.19; N, 15.37; Found: C, 65.83; H, 7.79; N, 15.23.

3. (8β)-N-[(4-Pyridinyl)methyl]-1-isopropyl-6-methylergoline-8-carboxamide, 35% yield, m.p.=225°–227° C.

Analysis for $C_{25}H_{30}N_4O$: Calc.: C, 74.60; H, 7.51; N, 13.92; Found: C, 74.41. H, 7.39; N, 13.71.

4. (8β)-N-[(3-Pyridinyl)methyl]-6-methyl-1-(2-methylpropyl)ergoline-8-carboxamide, 61% yield, m.p. 202°–203° C.

Analysis for $C_{26}H_{32}N_4O$: Calc. C, 74.97: H, 7.74; N, 13.45: Found: C, 75.03; H, 7.92; N, 13.38.

5. (8β)-N-[(3-Pyridinyl)methyl]-6-methyl-1-propylergoline-8-carboxamide, 53% yield, m.p. 206°–207° C.

Analysis for $C_{25}H_{30}N_4O$: Calc.: C, 74.60; H, 7.51; N, 13.92; Found: C, 74.40; H, 7.55; N, 13.65.

6. (8β)-N-[2-(2-Pyridinyl)ethyl]-6-methyl-1-propylergoline-8-carboxamide, 51% yield, m.p. 167.5°–168.5° C.

Analysis for $C_{26}H_{32}N_4O$: Calc.: C, 74.97; H, 7.74; N, 13.45; Found: C, 74.77; H, 8.01; N, 13.67.

7. (8β)-N-[2-(2-Pyridinyl)ethyl]-6-methyl-1-(2-methylpropyl)ergoline-8-carboxamide hydrate (4:1), 65% yield, m.p. 162°–163° C.

Analysis for $C_{27}H_{34}N_4O.0.25\ H_2O$: Calc.: C, 74.53; H, 7.99; N, 12.87; Found: C, 74.44; H, 7.82; N, 12.60.

8. (8β)-N-[2-(2-Pyridinyl)ethyl]-6-methyl-1-(1-methylethyl)ergoline-8-carboxamide dimaleate hydrate, m.p. 102°–107° C.

Analysis for $C_{26}H_{32}N_4O.2(C_4H_4O_4).0.6\ H_2O$: Calc.: C, 61.91; H, 6.29; N, 8.49; Found: C, 61.72; H, 6.13; N, 8.27.

9. (8β)-N-[(2-Pyridinyl)methyl]-6-methyl-1-(1-methylethyl)ergoline-8-carboxamide dimaleate hydrate, m.p. 104°–110° C.

Analysis for $C_{25}H_{30}N_4O.2(C_4H_4O_4).0.8\ H_2O$ Calc.: C, 61.06; H. 6.14: N, 8.63; Found: C, 61.10; H, 5.91; N, 8.47.

10. (8β)-N-[(3-Pyridinyl)methyl]-6-methyl-1-(1-methylethyl)ergoline-8-carboxamide maleate, m.p. 191°–196° C.

Analysis for $C_{25}H_{30}N_4O.C_4H_4O_4$: Calc.: C, 67.16; H, 6.61; N, 10.80; Found: C, 67.76; H, 6.64; N, 10.66.

11. (8β)-N-[2-(3-Pyridinyl)ethyl]-6-methyl-1-(1-methylethyl)ergoline-8-carboxamide dioxalate, yield, m.p. 163°–164° C.

Analysis for $C_{26}H_{32}N_4O.2(C_2H_2O_4)$: Calc.: C, 60.39; H, 6.08; N, 9.39; Found: C, 57.68; H, 5.73; N, 9.15.

12. (8β)-N-[3-Pyridinyl)propyl]-8-methyl-1-(1-methylethyl)ergoline-8-carboxamide dioxalate, yield, m.p. 125°–127° C.

Analysis for $C_{27}H_{34}N_4).2(C_2H_2O_4)$: Calc.: C, 60.99; H, 6.27; N, 9.17; Found: C, 57.91; H, 6.15; N, 9.59.

13. (8β)-N-[4-(3-Pyridinyl)butyl]-6-methyl-1-(1-methylethyl)ergoline-8-carboxamide dioxalate, 51% yield, m.p. 105°–107° C.

Analysis for $C_{28}H_{36}N_4O.2(C_2H_2O_4)$: Calc.: C, 61.53; H, 6.45; N, 8.97; Found: C, 57.24; H, 6.08; N, 9.40.

EXAMPLE 14

(8β)-N-[(3-Pyridinyl)methyl]-1,6-dimethylergoline-8-carboxamide

One gram of 1,6-dimethylergoline-8-carboxylic acid was slurried with 40 ml of dimethylformamide under a nitrogen atmosphere. The mixture was cooled by means of an external ice/acetone bath. To the slurry were added 700 mcl of phosphorous oxychloride in dropwise fashion keeping the temperature below 0° C. After stirring for 30 minutes, 800 mcl of 3-(aminomethyl)pyridine were added. After stirring an additional two hours, the mixture was poured into approximately 200 ml of dilute ammonium hydroxide and extracted with ethyl acetate. The organic layer was washed with water and a saturated sodium chloride solution, dried over sodium sulfate, and concentrated in vacuo. The residue was crystallized from ethyl acetate/hexane to provide 700 mg of the desired title product, m.p. 185°–187° C.

Analysis for $C_{23}H_{26}N_4O$: Calc.: C, 73.77; H, 6.99; N, 14.96; Found: C, 72.91; H, 6.64; N, 14.38.

EXAMPLES 15–17

The following compounds were prepared according to the procedure of Example 14 employing the appropriate ergoline-8-carboxylic acid and corresponding amine.

15. (8β)-N-[2-(2-Pyridinyl)ethyl]-1,6-dimethylergoline-8-carboxamide, 46% yield, m.p. 190° C.

Analysis for $C_{24}H_{28}N_4O$: Calc.: C, 74.20; H, 7.26; N, 14.42; Found: C, 72.96; H, 7.12; N, 13.71.

16. (8β)-N-[2-(2-Pyridinyl)ethyl]-1-ethyl6-methylergoline-8-carboxamide, 46% yield, m.p. 169°–170° C.

Analysis for $C_{25}H_{30}N_4O$: Calc.: C, 74.60; H, 7.51; N, 13.92; Found: C, 74.32; H, 7.23; N, 13.70.

17. (8β)-N-3-Pyridinyl)methyl]-6-methyl-1-ethylergoline-8-carboxamide, 61% yield, m.p. 187°–188° C.

Analysis for $C_{24}H_{28}N_4O$: Calc.: C, 74.20; H, 7.26; N, 14.42; Found: C 73.95; H, 7.31; N, 14.12.

As noted above, the compounds of the present invention are useful for blocking $5HT_2$ receptors in mammals having an excess of serotonin centrally or peripherally. As such, this invention also provides a method of blocking $5HT_2$ receptors which comprises administering to a mammal having an excess of serotonin centrally or peripherally a $5HT_2$ blocking dose of a compound of the invention. This method is potentially useful in treating disease states in which an excess of circulating serotonin is a major contributing cause. These disease states include hypertension, thrombosis, complications arising from atherosclerosis, migraine, vasospasm (both coronary and cerebral), ischemia, depression, anxiety, schizophrenia, sexual dysfunction, sleep disorders and appetite disorders.

The compounds of the invention show relatively slight affinity for other receptors such as $\alpha_1$, $\alpha_2$, $\beta$, histamine, acetylcholine and the like receptors, and thus are highly selective in their action. In mammals, hypertension may be mediated through $5HT_2$ receptors. Thus, compounds of the invention will lower blood pressure in humans as does ketanserin, another $5HT_2$ blocker, but without the side effects attributable to alpha adrenergic receptor blockade of ketanserin.

In carrying out the methods of the invention, a compound of the invention is administered orally or parenterally to a mammal with an excess of circulatory serotonin in which mammal it is desirable to block $5 HT_2$ receptors in order to alleviate symptoms attributable to excessive serotonin levels such as migraine or depression. For parenteral administration, a water soluble salt of the drug is dissolved in an isotonic salt solution and administered by the intravenous route. For oral administration, a pharmaceutically-acceptable salt of the drug is mixed with standard pharmaceutical excipients such as starch and loaded into capsules or made into tablets, each containing about 0.1 to about 100 mg of active drug. Dosage levels of from about 0.01–1000 mg/kg are effective in blocking $5HT_2$ receptors. Thus, the oral dosage would be administered 2–4 times per day, giving a daily dosage range of about 0.003 to about 10.0 mg/kg per day. It is a special feature of the compounds of this invention that very potent blockers of the $5HT_2$ receptor and are also considerably more water soluble than related agents.

In order to demonstrate that the compounds of the invention block $5HT_2$ receptors, the compounds were evaluated in pithed rats previously dosed with serotonin (5HT). In control animals, an increase in mean arterial pressure (MAP) is seen when 1 mg/kg of 5HT is administered i.v. 60 minutes after the oral administration of distilled water as compared to the same animals before 5HT administration. This pressor response to 5HT can be blunted by administering a compound of Formula I in water by gavage 60 minutes prior to 5HT administration. The animals are pithed 45 minutes after administration of vehicle or test compound and administered the 5HT fifteen minutes thereafter. This procedure is similar to that reported by Cohen et al., *J. Cardiovascular Pharmacology,* 11 (51), 525 (1988) except that groups of 3 or 4 normotensive rats were used for each experimental condition instead of spontaneously hypertensive rats. The results of testing are reported in Table 1.

TABLE 1

| | Inhibition of 5HT Induced Pressor Response in Pithed Rats | |
|---|---|---|
| | Increase in MAP (mm mercury)* Dose mg/kg p.o. | |
| Example No. | 3.0 | 0.1 |
| 1 | | 100.5 |
| 2 | | 103.9 |
| 3 | −7.8 | |
| 4 | | 111.6 |
| 5 | | 100.0 |
| 6 | | 111.9 |
| 7 | | 110.3 |
| 8 | 2.8 | 35.6 |
| 9 | 20.3 | 89.4 |
| 10 | 6.1 | 80.3 |
| 11 | | 111.1 |
| 12 | | 101.9 |
| 13 | | 89.7 |
| 14 | | 92.5 |
| 15 | | 106.1 |
| 16 | | 69.2 |

*Compounds administered orally in water 60 minutes prior to 5HT administration. Animals were pithed 15 minutes prior to 5HT administration. Increase measured after 1.0 mg/kg 5HT administration i.v. compared with same animals before administration of 5HT. Seven control animals orally given 5 ml/kg distilled water instead of compound had an average increase in MAP of 104.5 mm mercury.

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form"

refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
|---|---|
| 8β-N—[(3-pyridinyl)methyl]-l-isopropyl-6-methylergoline-8-carboxamide | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| (8β)-N—([2-(2-pyridinyl)ethyl]-l-isopropyl-6-methylergoline-8-carboxamide | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
|---|---|
| (8β)- 1—[(2-pyridinyl)methyl]-l-isopropyl-6-methylergoline-8-carboxamide | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

Formulation 4

Tablets each containing 60 mg of active ingredient are made as follows:

| (8β)-N—methyl-N—[(1H—imidazol-1-yl)-methyl]-l-isopropyl-6-methyl-ergoline-8-carboxamide | 60 mg |
|---|---|
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| (8β)-N—[(3-(1H-imidazol-4-yl)propyl]-1-isopropyl-6-n-propylergoline-8-carboxamide maleate | 80 |
|---|---|
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| (8β)-N—[(4-pyridinyl)methyl]-l-isopropyl-6-methylergoline-8-carboxamide | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| (8β)-N—[(3-pyridinyl)methyl-l-isopropyl-6-methylergoline-8-carboxamide | 50 mg |
|---|---|
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| (8β)-N—[2-(2-pyridinyl)ethyl]-1-isopropyl-6-methylergoline-8-carboxamide hydrochloride | 100 mg |
| isotonic saline | 1000 ml |

The solution of the above ingredients is administered intravenously at a rate of 1 ml per minute to a subject in need of treatment for sexual dysfunction.

We claim:

1. A compound of the formula wherein:
$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is pyridinyl or imidazolyl;
alk is a divalent organic radical derived from a straight or branched $C_1$-$C_5$ alkane;
or a pharmaceutically acceptable acid addition salt thereof.

2. A compound of claim 1 wherein $R^1$ is isopropyl.
3. A compound of claim 2 wherein $R^2$ is methyl.
4. A compound of claim 3 wherein $R^3$ is hydrogen.
5. A compound of claim 4 wherein alk is —CH$_2$— or —CH$_2$CH$_2$—.
6. The compound of claim 5 which is (8β)-N-[(3-pyridinyl)methyl]-1-isopropyl-6-methylergoline-8-carboxamide or a pharmaceutically-acceptable salt thereof.
7. The compound of claim 5 which is (8β)-N-[2-(2-pyridinyl)ethyl]-1-isopropyl'-6-methylergoline-8-carboxamide or a pharmaceutically-acceptable salt thereof.
8. A method of blocking 5HT$_2$ receptors which comprises administering to a mammal having an excess of serotonin centrally or peripherally a 5HT$_2$ blocking dose of a compound of claim 1.
9. A method of claim 8 wherein $R^1$ is isopropyl.
10. A method of claim 9 wherein $R^2$ is methyl.
11. A method of claim 10 wherein $R^3$ is hydrogen.
12. The method of claim 11 wherein the compound is (8β)-N-(3-pyridinyl)methyl]-1-isopropyl-6-methylergoline-8-carboxamide or a pharmaceutically acceptable salt thereof.
13. The method of claim 11 wherein the compound is (8β)-N-[2-(2-pyridinyl)ethyl]-1-isopropyl-6-methylergoline-8-carboxamide or a pharmaceutically-acceptable salt thereof.
14. A method of treating hypertension in mammals which comprises administering to a hypertensive mammal a hypotensive dose of a compound of claim 1.
15. A method of claim 14 wherein $R^1$ is isopropyl.
16. A method of claim 15 wherein $R^2$ is methyl.
17. A method of claim 16 wherein $R^3$ is hydrogen.
18. The method of claim 17 wherein the compound is (8β)-N-[(3-pyridinyl)methyl]-1-isopropyl-6-methylergoline-8-carboxamide or a pharmaceutically-acceptable salt thereof.
19. The method of claim 17 wherein the compound is (8β)-N-[2-(2-pyridinyl)ethyl]-1-isopropyl-6-methylergoline-8-carboxamide or a pharmaceutically-acceptable salt thereof.
20. A pharmaceutical formulation comprising a compound of claim 1 and a pharmaceutically acceptable carrier, diluent or excipient therefor.
21. A method of claim 20 wherein $R^1$ is isopropyl.
22. A method of claim 21 wherein $R^2$ is methyl.
23. A method of claim 22 wherein $R^3$ is hydrogen.
24. The formulation of claim 23 wherein the compound is (8β)-N-[(3-pyridinyl)methyl]-1-isopropyl-15 6-methylergoline-8-carboxamide or a pharmaceutically-acceptable salt thereof.
25. The formulation of claim 23 wherein the compound is (8β)-N-2-(2-pyridinyl)ethyl]-1-isopropyl-6-methylergoline-8-carboxamide or a pharmaceutically-acceptable salt thereof.

UNITED STATES PATENT AND TRADEMARK OFFICE
CERTIFICATE OF CORRECTION

PATENT NO. : 4,902,691

DATED : February 20, 1990

INVENTOR(S) : Marlene L. Cohen et al.

It is certified that error appears in the above-identified patent and that said Letters Patent is hereby corrected as shown below:

Column 6, line 3, "Ns is" should read -- $N^6$ is --.

Column 10, line 26, "dioxalate, yield," should read -- dioxalate, 62% yield, --.

Column 10, line 28, "$C_{27}H_{34}N_4).2(C_2H_2O_4)$:" should read -- $C_{27}H_{34}N_4O.2(C_2H_2O_4)$: --.

Column 16, line 37, "A method of" should read -- A formulation of --.

Column 16, line 38, "A method of" should read -- A formulation of --.

Column 16, line 39, "A method of" should read -- A formulation of --.

Column 16, line 41, "-1-isopropyl-15 6-" should read -- -1-isopropyl-6- --.

Column 16, line 45, "(8β)-N-2-(2-" should read -- (8β)-N-[2-(2- --.

Signed and Sealed this

Nineteenth Day of March, 1991

*Attest:*

HARRY F. MANBECK, JR.

*Attesting Officer*   *Commissioner of Patents and Trademarks*